(12) United States Patent
Rand

(10) Patent No.: US 7,703,620 B2
(45) Date of Patent: Apr. 27, 2010

(54) CHAIN LINKED CAPSULES

(75) Inventor: Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1081 days.

(21) Appl. No.: 10/551,256

(22) PCT Filed: Apr. 14, 2004

(86) PCT No.: PCT/EP2004/004007

§ 371 (c)(1),
(2), (4) Date: Sep. 27, 2005

(87) PCT Pub. No.: WO2004/091703

PCT Pub. Date: Oct. 28, 2004

(65) Prior Publication Data

US 2006/0191931 A1    Aug. 31, 2006

(30) Foreign Application Priority Data

Apr. 17, 2003    (GB)    ................... 0308969.5

(51) Int. Cl.
B65D 21/02    (2006.01)
(52) U.S. Cl. .............. 220/23.4; 220/23.2; 220/23.8; 220/23.83; 220/23.86
(58) Field of Classification Search ........... 220/23.8, 220/23.83, 23.86, 4.26, 4.27, 4.01, 4.22, 220/23.2, 507, 4.23
See application file for complete search history.

(56) References Cited

U.S. PATENT DOCUMENTS

| 1,410,556 | A | 3/1922 | Dorment |
| 2,103,520 | A | 12/1937 | Donnelly |
| 2,587,215 | A | 2/1952 | Priestly |
| 2,590,832 | A | 3/1952 | Brown |
| 2,642,063 | A | 6/1953 | Brown |
| 3,558,003 | A | 1/1971 | Jones |
| 4,095,587 | A | 6/1978 | Ishikawa |
| 4,391,590 | A | 7/1983 | Dougherty |
| 4,446,862 | A | 5/1984 | Baum et al. |
| 4,767,326 | A | 8/1988 | Bennett et al. |
| 4,815,625 | A | 3/1989 | Filhol et al. |
| 5,048,514 | A | 9/1991 | Ramella |
| 5,287,850 | A | 2/1994 | Haber et al. |
| 5,310,082 | A | 5/1994 | Coustenoble |
| 5,372,128 | A | 12/1994 | Haber et al. |
| 5,379,763 | A | 1/1995 | Martin |

(Continued)

FOREIGN PATENT DOCUMENTS

DE    837157 C    4/1952

(Continued)

OTHER PUBLICATIONS

U.S. Appl. No. 10/535,453, filed May 19, 2005.

*Primary Examiner*—Anthony Stashick
*Assistant Examiner*—Madison L Wright
(74) *Attorney, Agent, or Firm*—Dwight S. Walker

(57) ABSTRACT

Chain linked capsules comprising multiple capsules interconnected in a chain by chain links. The capsules comprise a sleeve and a piston whereby a powder product can be sealed within the capsule. The capsules are for use in inhalation devices, for example for entraining a dose of an inhalable pharmaceutical powder product to a patient's respiratory tract.

13 Claims, 4 Drawing Sheets

U.S. PATENT DOCUMENTS

| | | | |
|---|---|---|---|
| 5,562,918 A | 10/1996 | Stimpson | |
| 5,595,175 A | 1/1997 | Malcher et al. | |
| 5,617,971 A | 4/1997 | Eason et al. | |
| 5,673,686 A | 10/1997 | Villax et al. | |
| 5,720,406 A * | 2/1998 | Fassbind et al. | 220/23.4 |
| 5,727,546 A | 3/1998 | Clarke et al. | |
| 5,769,070 A | 6/1998 | Frati et al. | |
| 5,778,873 A | 7/1998 | Braithwaite | |
| 5,797,392 A | 8/1998 | Keldmann et al. | |
| 5,881,721 A | 3/1999 | Bunce et al. | |
| 5,896,855 A | 4/1999 | Hobbs et al. | |
| 5,924,417 A * | 7/1999 | Braithwaite | 128/203.15 |
| 6,102,036 A | 8/2000 | Slutsky et al. | |
| 6,109,261 A | 8/2000 | Clarke et al. | |
| 6,357,490 B1 | 3/2002 | Johnston et al. | |
| 6,470,884 B2 | 10/2002 | Horlin | |
| 6,503,084 B2 | 1/2003 | Evers et al. | |
| 6,708,884 B1 | 3/2004 | Su et al. | |

FOREIGN PATENT DOCUMENTS

| | | |
|---|---|---|
| EP | 0406893 A1 | 1/1991 |
| EP | 0928618 B1 | 7/1999 |
| EP | 1245243 A1 | 10/2002 |
| GB | 367560 A | 2/1932 |
| GB | 367580 | 2/1932 |
| GB | 2323042 A | 9/1998 |
| GB | 2323942 A | 10/1998 |
| GB | 2340758 | 3/2000 |
| WO | 8902289 A1 | 3/1989 |
| WO | 9531238 | 11/1995 |
| WO | 9958180 | 11/1999 |
| WO | 0001437 A1 | 1/2000 |
| WO | 0107107 A2 | 2/2001 |
| WO | 0117595 A1 | 3/2001 |
| WO | 0128617 A | 4/2001 |
| WO | 01/30430 | 5/2001 |
| WO | 0213897 A2 | 2/2002 |
| WO | 02096489 A1 | 12/2002 |
| WO | 02098495 A1 | 12/2002 |
| WO | 03030974 A1 | 4/2003 |
| WO | 03035151 A1 | 5/2003 |
| WO | 03047670 A1 | 6/2003 |
| WO | 03061743 A1 | 7/2003 |
| WO | 2004/045688 | 6/2004 |
| WO | 2004/045688 A1 | 6/2004 |

* cited by examiner

CHAIN LINKED CAPSULES

CROSS-REFERENCE TO RELATED APPLICATIONS

This application is filed pursuant to 35 U.S.C. § 371 as a United States National Phase Application of International Application No. PCT/EP2004/004007 filed Apr. 14, 2004, which claims priority from GB 0308969.5 filed Apr. 17, 2003.

FIELD OF THE INVENTION

The present invention relates to chain linked capsules and is particularly, although not exclusively, concerned with such capsules which are adapted to contain therein a powder product, for example a medicinal powder product for a person to inhale using a dry powder inhalation device ("DPI" for short).

BACKGROUND OF THE INVENTION

DPIs are well established for use in treating respiratory diseases. As an example, there is the DISKUS® device of GlaxoSmithKline. In general, the pharmaceutical composition is formulated as a respirable powder product and the powder product is divided into a plurality of unit doses, each dose contained in its own sealed enclosure, for example in blisters on a dosing strip. When using prior art inhalation devices, an enclosure on a dosing strip in the inhalation device is opened by an opening mechanism of the inhalation device and the powder dose in the enclosure can then be entrained into a patient's respiratory tract by an airflow generated through the device by the patient inhaling at a mouthpiece of the device.

Some sealed enclosures used in DPIs are difficult to fill with a unit dose of the pharmaceutical powder product. Therefore there has been a tendency to make the enclosures bigger than they need to be, and adding a filler to the pure drug powder, such as lactose powder, to bulk out the powder product. The filling of larger enclosures is easier. However, GB0227128.6, filed 20 Nov. 2002, and PCT/EP03/13074 claiming priority therefrom, provides a capsule for holding a powder product which has a mechanism for facilitating the filling of it with the powder product.

The capsule disclosed in GB0227128.6 and PCT/EP03/13074 will generally be small enough to dispense active ingredients without the need to bulk out the powder with a lactose or other filler as much as before or even at all. Due to its small size, the capsule is referred to as a "microcapsule".

The handling of the capsule, however, can be difficult or fiddly. The present invention facilitates the handling of the capsule, in particular once filled, for example to make it easier to manipulate a number of them when loaded in a DPI.

SUMMARY OF THE INVENTION

The present invention provides chain linked capsules. Preferably the present invention provides chain linked microcapsules, for example of a length of no more than about 15 mm, preferably no more than about 6 mm, and a width of no more than about 8 mm, preferably no more than about 5 mm. Preferably the chain linked capsules form a loop, e.g. an endless loop like a bicycle chain.

By chain linking the capsules (or microcapsules), they are easier to manipulate during filling, or during use in a DPI, than separate capsules or microcapsules.

The present invention further provides a capsule and a chain link for the capsule. Preferably the chain link is engageable with the capsule, for example by insertion of a protrusion of the chain link into an opening in the capsule. However it may be integral with the capsule or it may be engaged with the capsule.

Preferably the chain link extends from the capsule. Preferably it extends from a base of the capsule.

Preferably the capsule is generally cylindrical.

Preferably the chain link extends generally radially outward from the capsule.

Preferably the capsule comprises a chamber for containing a powder product.

Preferably the capsule comprises a sleeve which is provided with an internal chamber for holding a powder product within the capsule.

Preferably the sleeve comprises a first opening at a first end thereof and a second opening at an opposite end thereof.

Preferably the capsule comprises the sleeve and a piston.

Preferably the capsule comprises two chambers separated by a flange portion within the sleeve, the first of the chambers being for containing the powder product.

Preferably the sleeve is a single piece component.

Preferably the piston is adapted to extend within the sleeve from the first end, through the first chamber and the flange portion, and into the second chamber.

Preferably the piston comprises a cap and a rod. Preferably these parts are integrally formed.

Preferably the piston can seal the first chamber by forming a seal against the first opening and the flange portion.

Preferably the sleeve and the piston are adapted to be displaced between a discharging position or state in which both the chamber of the capsule that is adapted to contain a powder product is open to the outside environment and a vent provided in the base of the chamber is open for allowing powder product from within the chamber to be sucked out of the chamber through the first opening to the outside environment and a sealing state in which both the chamber is sealed from the outside environment and the vent is closed.

Preferably the base is the flange portion that separates the two chambers and the vent is provided through the flange portion.

Preferably, in the sealing state, the piston closes the vent to isolate the two chambers from each other.

Preferably the capsule can be placed into a third state in which the chamber is open to the outside environment at the first opening and there is a partial seal at the vent. This partial seal will be gas pervious but will entrap powder product, thereby enabling a vacuum to be applied at the vent to create an airflow from the first opening, through the chamber, towards the vent for entraining powder product from a powder product cloud in the outside environment into the chamber. The powder product will not pass beyond the vent, thereby filling the chamber with powder product.

Preferably the partial seal at the vent is formed with the piston extending through the flange portion between the two chambers. Preferably, the piston has a circumferential array of longitudinal channels formed in the portion of the outer surface of the piston that is within the flange portion.

Preferably the second opening of the sleeve is adapted to engage with a correspondingly sized protrusion on a chain link for rotatably connecting the capsule to the chain link.

Preferably the protrusion is a tubular portion having a hole therethrough.

Preferably the chain link is pivotally connected to the capsule, or another capsule, at one end of the chain link.

Preferably the chain link is pivotally connectable to capsules at both ends of the chain link.

Preferably a flange extends outwardly from the second end of the sleeve of the capsule. Preferably a tubular portion is provided at an outermost end of the flange. The flange may be integrally formed with the sleeve.

Preferably the tubular portion has a diameter that is substantially equal to or slightly greater than the diameter of the second opening of the capsule.

Preferably the tubular portion is inserted into an open end of an adjacent, identical, capsule to form chain linked capsules.

Preferably the connection is a push fit. However, the connection may be a loose fit.

Preferably the inside diameter of the tubular portion is larger than the distal end of the piston.

The chain link may be a separately formed component comprising two tubular portions.

Preferably the two tubular portions are provided at the ends of a flange. Preferably the flange extends between the bases of the tubular portions.

Preferably a first tubular portion is of a first diameter and the second tubular portion is of a second diameter.

Preferably both tubular portions are hollow.

Preferably the second tubular portion has an internal diameter corresponding generally to the outside diameter of the first tubular portion.

Preferably the first tubular portion of a first chain link fits within a second tubular portion of an adjacent, identical, chain link.

Preferably the second tubular portion has an outside diameter corresponding generally with the diameter of the second opening of the capsule.

Preferably a plurality of capsules and chain links are connected together to form chain linked capsules.

Preferably chain linked capsules are provided within a channel. The channel may be a closed channel, i.e. with both a base and a roof, or the like, and/or an endless channel.

Preferably the capsules and chain links are made of a plastics material. Preferably they are moulded.

The present invention further provides an inhalation device having chain linked, medicinal powder-containing, capsules. Preferably, the capsules are linked in an endless chain.

Embodiments of the present invention will now be described, by way of example only, with reference to the accompanying drawings in which:

DETAILED DESCRIPTION

Figure 1:
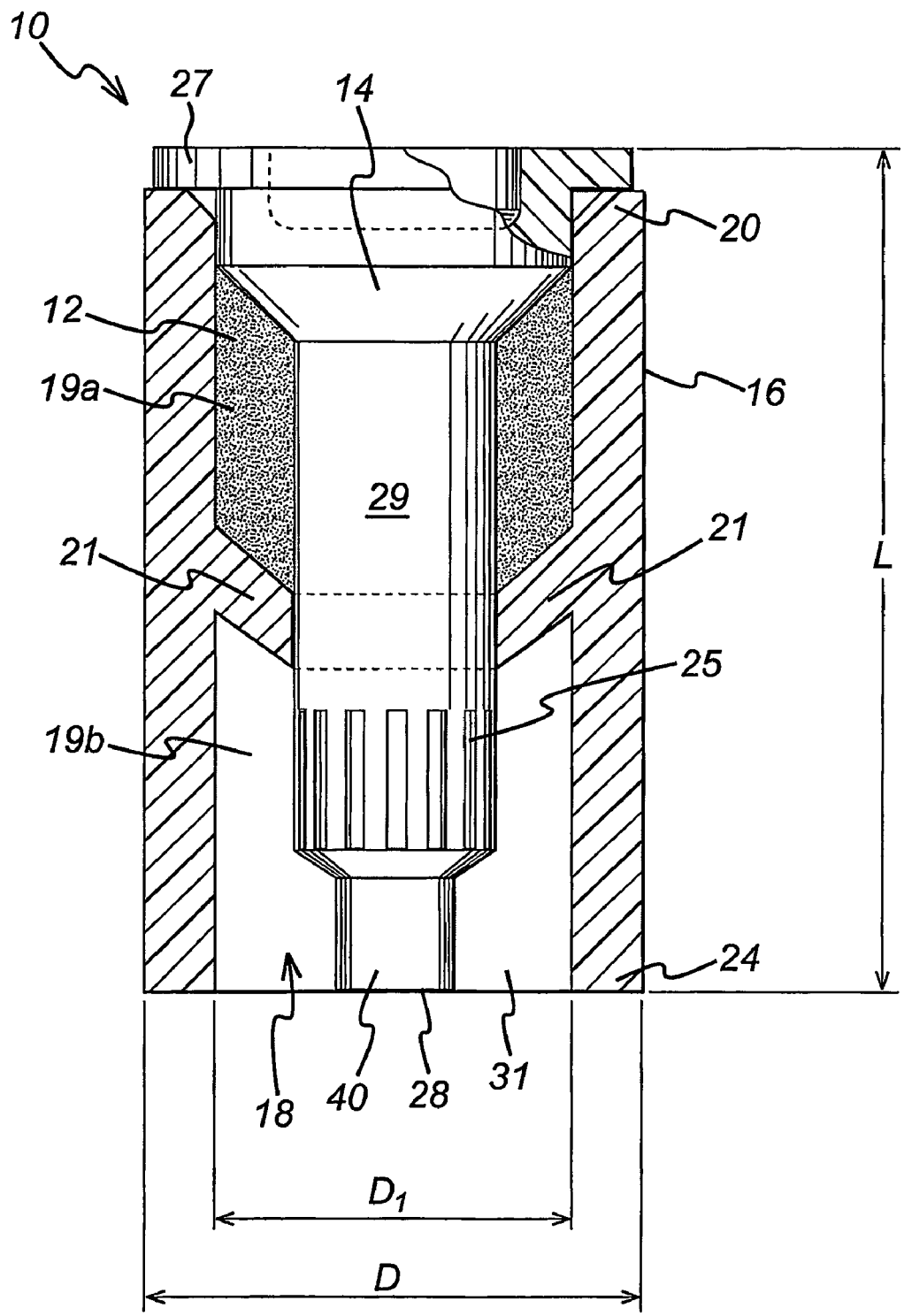
FIG. 1 is a part sectional side view of a capsule for a powder product as disclosed in GB0227128.6 and PCT/EP03/13074 for use in the present invention with the powder product contained in a sealed chamber defined between a piston and a sleeve.
Figure 2:
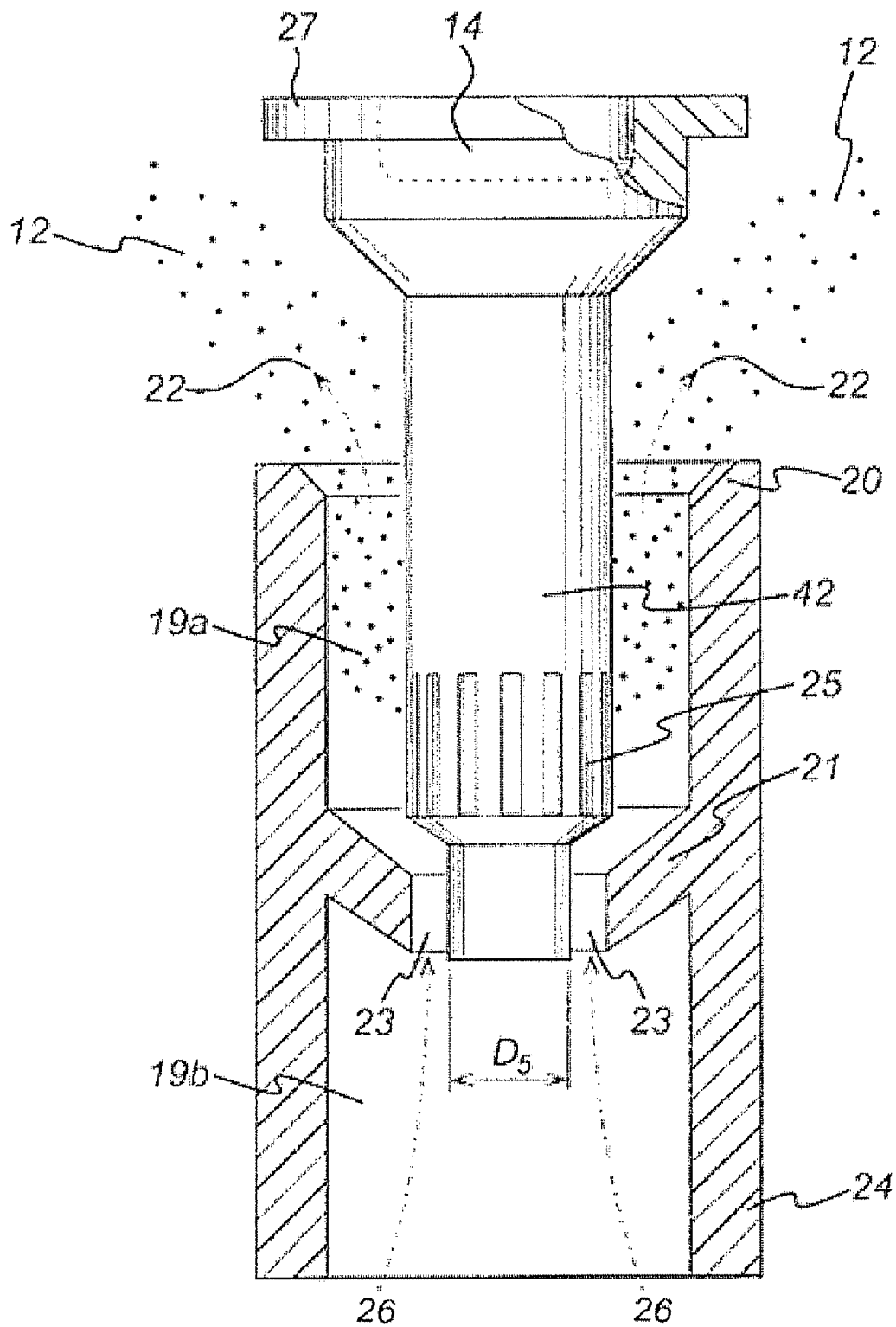
FIG. 2 is a cross-sectional view of the capsule of FIG. 1 in a discharge position relative to the sleeve.

Referring to FIGS. 1 and 2 there is shown a generally cylindrical capsule 10 filled with a powder product 12. The capsule 10 has particular application for dry powder products, more particularly for holding a unit dose of a dry powder pharmaceutical formulation or medicament for inhalation by a patient. The capsule 10 may be used in a dry powder inhalation device (a DPI).

The capsule 10 of FIGS. 1 and 2 is described in detail in GB0227128.6 and PCT/EP03/13074, the entire contents of which are incorporated herein by way of reference.

The capsule 10 comprises a piston 14 and a sleeve 16.

The sleeve 16 is a generally tubular or cylindrical member that defines a generally cylindrical passage 18 therethrough.

The passage 18 defines two chambers 19a, 19b separated by a flange portion 21. The passage 18 has two ends 20, 24. The flange portion 21 is between the two ends 20, 24.

The piston 14 can positioned selectively within the sleeve 16 to provide various states for the capsule 10: a filling state, a sealing state and a dispensing state.

A sealing state is shown in FIG. 1. The first chamber 19a is sealed closed; the first end 20 of the passage 18 and the flange portion 21 are both sealed by the piston 14. The second end 24 of the passage 18, however, is open.

A dispensing state is shown in FIG. 2. The first chamber 19a is no longer sealed. The first end 20 is open and a vent 23 between the flange portion 21 and the piston 14 is open. The second end 24 also still is open. Powder 12 contained within the first chamber 19a can therefore be vented 22 from within the capsule 10 through the first end 20 to the outside environment.

In a filling state, not shown, the piston 14 is positioned halfway between its positions in the dispensing state and the sealing state. In this position, the first end 20 of the passage 18 will still be open, but the vent 23 between the piston 14 flange portion 21 will be partially sealed (see GB0227128.6 and PCT/EP03/13074). The piston 14 has a circumferential array of longitudinal channels 25 formed in the portion of the outer surface of the piston 14 that will lie within the flange portion 21 in the filling state. These channels 25 allow air to pass through the vent 23, but will not allow powder 12 to pass through the vent 23. Therefore, the first chamber 19a can be filled by drawing air having powder 12 dispersed therein through the passage 18 extending through the capsule 10 from the first end 20 of the passage 18 to the second end 24 of the passage, when the capsule 10 is in its filling state.

The piston 14 comprises a cap 27 and a rod 29. The cap 27 is for sealing the first end 20 of the passage 18 when the piston 14 is pushed fully into the passage 18, as shown in FIG. 1. The rod 29 extends axially through the passage 18 and is for selectively opening the vent 23 in the flange portion 21.

The rod 29 comprises various portions. Starting at its distal end 28 there is a narrowed portion 40. Then there is the circumferential array of longitudinal channels 25. Finally there is a smooth sided piston portion 42. These, when positioned within the flange portion 21, select the sealing state of the vent 23 in the flange portion 21: open, partially sealed and sealed, respectively.

The length of the rod 29 is such that, in the sealing state, the distal end 28 of the piston 14 does not protrude beyond the second end 24 of the sleeve 16.

The rod and the passage are generally round in shape. Other shapes may, however, be used. For a round shape, the distal end 14 of the rod 29 has an outer diameter $D_5$ that is much smaller than the inner diameter $D_1$ of the passage 18 at the second end 24 of the sleeve 16. This means that there is an annular space 31 at the second end 24 of the sleeve 16 even when the piston 14 is fully pushed into the sealing state shown in FIG. 1. This annular space 31, in accordance with the present invention, allows a chain link to be used to form chain linked capsules.

Figure 3:
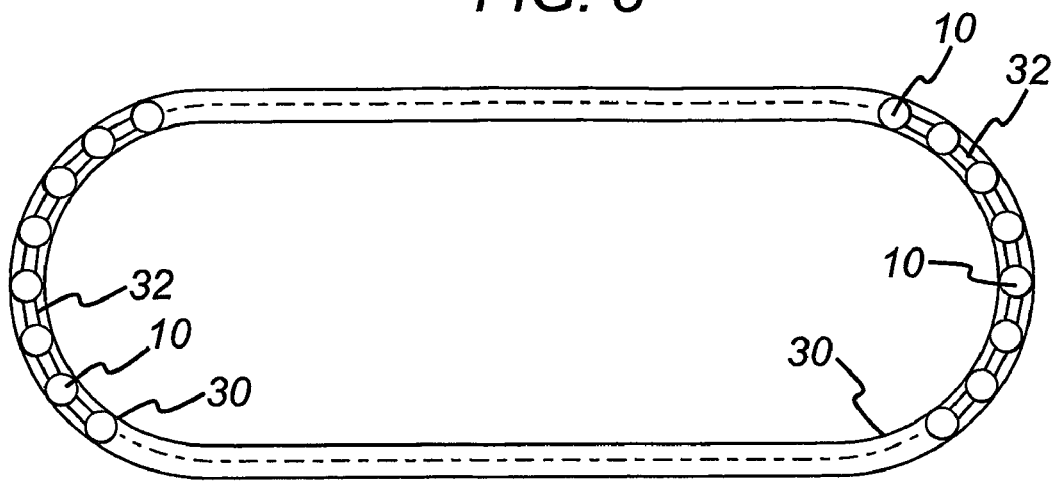
FIG. 3 shows a plurality of capsules in accordance with the present invention in an endless channel.

FIG. 3 shows a plurality of chain linked capsules 10 in an endless channel 30 such as one in a DPI, not shown. Such an endless channel 30 may be provided for retaining a plurality of capsules 10 for use, one at a time, by the DPI.

Figure 4:
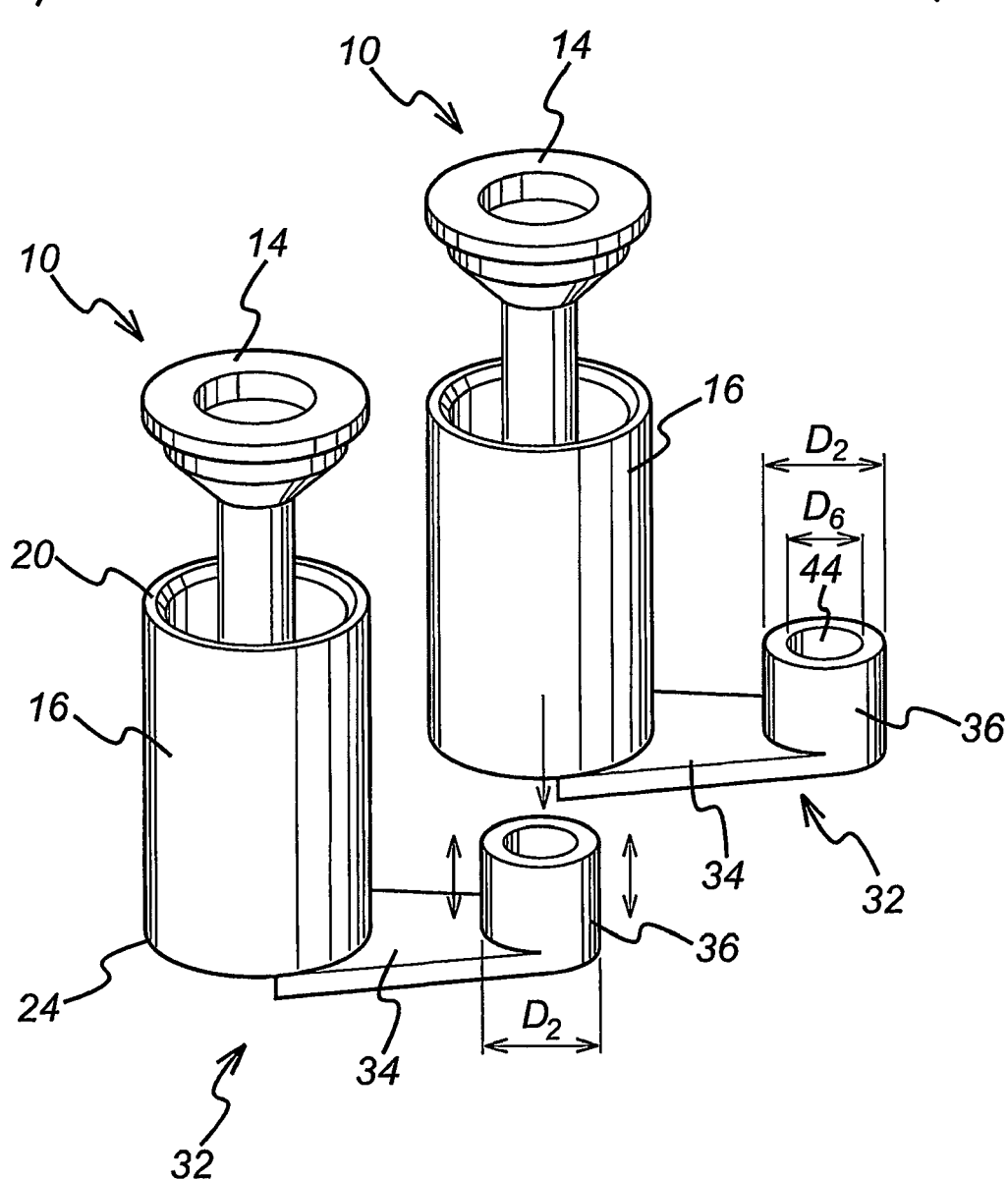
FIG. 4 shows a pair of capsules in accordance with the present invention.

Referring to FIG. 4, a preferred arrangement for the chain link 32 is shown.

The capsule 10 is generally as described with reference to FIGS. 1 and 2. However, a flange 34 extends outwardly from the second end 24 of the sleeve 16 of the capsule 10 to a tubular portion 36. The flange 34 and the tubular portion 36 form the chain link 32.

Figure 5:
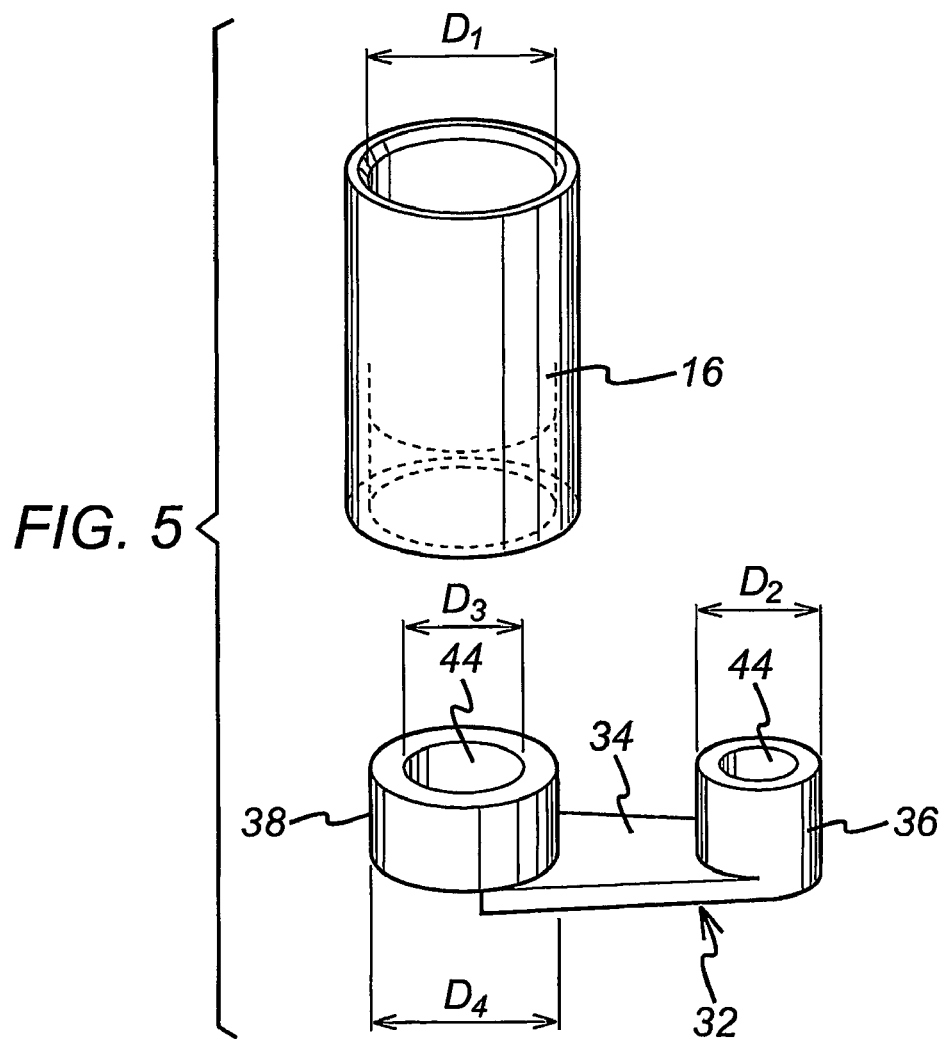
FIG. 5 shows an alternative embodiment of the present invention.

The flange 34 is integrally formed with the sleeve 16. Referring to FIG. 5, however, the chain link 32 may be a separately formed component comprising a flange 34 and two tubular portions 36, 38.

Referring back to FIG. 4, the flange 34 has a tubular portion 36 at its outermost end. The tubular portion 36 has an outer diameter $D_2$ that is substantially equal to the inner diameter $D_1$ of the annular space 31, i.e. the passage 18 extending through the sleeve 16 of the capsule 10. The tubular portion 36 can therefore be inserted into the annular space 31 at the second end 24 of an adjacent capsule 10 to chain link capsules together.

By making the connection a push fit between the tubular portion 36 and the annular space 31, relative rotation will still be achievable but the separation of the two connected capsules 10 will be difficult. Therefore, the chain linked capsules 10 would be able to travel along the endless channel 30 without being retained in the channel 30 from above.

Instead of a push fit connection, however, the capsules could be connected with a loose fit connection. This has the advantage of having a reduced resistance to flexing around the curves of the channel 30. However, there would be an increase in the tendency for adjacent capsules to separate, thereby breaking the chain link. By making the channel 30 a closed channel, i.e. with both a base and a roof, or the like, relative axial movement between adjacent capsules 10 would be eliminated. This would prevent inadvertent separation of adjacent capsules 10.

The tubular portion 36 has a hole 44 extending therethrough so that the distal end 28 of the piston 14 can be fitted therein. The inside diameter $D_6$ of the hole 44 is larger than the outer diameter $D_5$ of the distal end 28 of the piston 14 so that relative rotation of adjacent capsules 10 will not cause the piston 14 to be rotated relative to its sleeve 16. This will help to prevent inadvertent dispensing of the powder 12 from within the capsule 10.

Referring again to FIG. 5, a separate chain link 32 is shown. In this embodiment, the chain link 32 has two tubular portions 36, 38. The two tubular portions 36, 38 are at opposed ends of a flange 34. The flange extends between the bases of the two tubular portions 36, 38.

The first tubular portion 36 has a first outside diameter $D_2$. The second tubular portion 38 has a second outside diameter $D_4$. Both tubular portions have holes 44 extending therethrough.

The second tubular portion 38 has an internal diameter $D_3$ corresponding generally to the outside diameter $D_2$ of the first tubular portion 36. The first tubular portion 36, therefore, has a smaller diameter than the second tubular portion 38 and it fits, rotatably, within a second tubular portion 38 of an adjacent chain link 32.

The second tubular portion 38 has an outside diameter $D_4$ corresponding generally with the inner diameter $D_1$ of the passage 18 in the sleeve 16 of the capsules 10. Therefore, the second tubular portion 38 of the chain link 32 will fit, rotatably, within the passage of the capsule 10. This will allow a plurality of capsules 10 and chain links 32 to be used to form chain linked capsules in accordance with the present invention.

The capsules 10 and chain links 32 are preferably made of a plastics material and they can be moulded, e.g. by injection moulding, micro moulding etc.

The capsules 10 may have a length L in the range of about 5 mm to about 15 mm, an outer diameter D in the range of about 3 mm to about 8 mm, and the passage 18 extending through the capsule 10 may have an inner diameter $D_1$ in the range of about 1 mm to about 6 mm. In other words, the capsules 10 may be microcapsules. Such capsules 10 are particularly suited for holding unit doses of pharmaceutical powder in the range of about 2 µg to about 30 mg. The capsules 10 may each contain a unit dose of pure active drug substance, or a blend of pure active drug substances, in the range of about 2 µg to about 250 µg (i.e. no bulk filler), or a bulked-out unit dose of pharmaceutical powder up to about 30 mg.

For a small unit dose of pharmaceutical powder, for instance in the range of about 2-250 µg, it is preferable for the capsule length L to be in the range of about 5 mm to about 6 mm, the outer capsule diameter D to be in the range of about 3 mm to about 5 mm, and the inner diameter $D_1$ of the passage 18 to be in the range of about 1 mm to about 3 mm, more preferably about 2 mm.

Appropriate medicaments for the inhalable pharmaceutical powder for use in the present invention may be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H)-benzothiazolone; adenosine 2a agonists, e.g. 2R,3R,4S,5R)-2-[6-Amino-2-(1S-hydroxymethyl-2-phenylethylamino)-purin-9-yl]-5-(2-ethyl-2H-tetrazol-5-yl)-tetrahydro-furan-3,4-diol (e.g. as maleate); $α_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are an anti-inflammatory agent (for example a corticosteroid or an NSAID), an anticholinergic agent, a $β_2$-adrenoreceptor agonists, an antinfective agent (e.g. an antibiotic or an antiviral) and an antihistamine. The medicament may be the sole medicament in the capsule or in combination with another medicament. Preferred combinations are based on the preferred medicament list above.

Preferred as a component of a medicament combination in the capsule are albuterol, salmeterol, fluticasone propionate and beclomethasone dipropionate and salts or solvates thereof, e.g., the sulphate of albuterol and the xinafoate of salmeterol.

A particularly preferred medicament combination for use in the capsule of the invention is a bronchodilator in combination with an anti-inflammatory. The bronchodilator is suitably a beta-agonist, particularly a long-acting beta-agonist (LABA). Suitable bronchodilators include salbutamol (e.g., as the free base or the sulphate salt), salmeterol (e.g., as the xinafoate salt) and formoterol (eg as the fumarate salt). The anti-inflammatory is suitably an anti-inflammatory steroid. Suitable anti-inflammatory compounds include a beclomethasone ester (e.g., the dipropionate), a fluticasone ester (e.g., the propionate) or budesonide or any salt or solvate thereof. One preferred combination is fluticasone propionate and salmeterol, or any salt or solvate thereof (particularly the xinafoate salt). A further preferred combination is budesonide and formoterol or any salt or solvate thereof (e.g. formoterol as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as a pure drug or together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient. The excipient may be included with the medicament via well-known methods, such as by admixing, co-precipitating and the like.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

It will of course be understood that the present invention has been described above purely by way of example. Modifications and developments may be made within the scope of the invention as defined in the claims appended hereto.

Moreover, use of terms such as "about" etc. in relation to values of parameters of the invention is meant to encompass the exact parameter value as well as minor deviations therefrom.

What is claimed is:

1. A capsule and a chain link for the capsule wherein the capsule comprises:
    an opening at an end thereof of a size corresponding with a protrusion on the end of the chain link and the protrusion is a tubular portion having a hole therethrough; and
    a sleeve which is provided with an internal chamber for holding a powder product within the capsule; and
    the internal chamber is a first chamber and the capsule comprises a flange portion which separates the first chamber from a second chamber, the second chamber being for connecting a chain link thereto.

2. The capsule and chain link of claim 1, wherein the capsule comprises a piston, the piston being adapted to extend within the sleeve from the first end thereof, through the first chamber and the flange portion, and into the second chamber.

3. A capsule and a chain link for the capsule wherein the capsule comprises:
    an opening at an end thereof of a size corresponding with a protrusion on the end of the chain link and the protrusion is a tubular portion having a hole therethrough; and
    a sleeve which is provided with an internal chamber for holding a powder product within the capsule; and
    a piston; and
    the sleeve and the piston are adapted to be displaced between
        a discharging position or state in which both the first chamber of the capsule is open to an outside environment and a vent provided in a base of the first chamber is open for allowing powder product from within the first chamber to be sucked out of the first chamber through the first opening to the outside environment and
        a sealing state in which both the first chamber is sealed from the outside environment and the vent is closed.

4. The capsule and chain link of claim 3, wherein the base of the first chamber is the flange portion and the vent is provided through the flange portion.

5. The capsule and chain link of claim 4, wherein, in the sealing state, the piston closes the vent to isolate the two chambers from each other.

6. The capsule and chain link of claim 2, wherein the piston has a circumferential array of longitudinal channels formed in a portion of the outer surface of the piston.

7. A capsule and a chain link for the capsule wherein the capsule comprises:
    an opening at an end thereof of a size corresponding with a protrusion on the end of the chain link and the protrusion is a tubular portion having a hole therethrough; and
    the chain link is pivotally connected to the capsule at one end of the chain link.

8. A capsule and a chain link for the capsule wherein the capsule comprises:
    an opening at an end thereof of a size corresponding with a protrusion on the end of the chain link and that the protrusion is a tubular portion having a hole therethrough; and
    the chain link is pivotally connectable to a capsule at both ends of the chain link.

9. The capsule and chain link of claim 8, wherein the tubular portion is a first tubular portion and the chain link comprises a second tubular portion and the first and second tubular portions are provided at ends of a flange.

10. The capsule and chain link of claim 9, wherein the tubular portions are of different outer diameters.

11. The capsule and chain link of claim 10, wherein both tubular portions are hollow, the second tubular portion having an internal diameter corresponding generally to the outside diameter of the first tubular portion.

12. The capsule and chain link of claim 11, wherein the second tubular portion has an outside diameter corresponding with the diameter of the opening.

13. A plurality of capsules and chain links for the capsules wherein each capsule comprises:
    an opening at an end thereof of a size corresponding with a protrusion on the end of each chain link and the protrusion is a tubular portion having a hole therethrough; and
    the chain links are pivotally connected to the capsules to form chain linked capsules.

* * * * *